United States Patent [19]

Deniega et al.

[11] Patent Number: 5,460,493

[45] Date of Patent: Oct. 24, 1995

[54] ORGANIZER FRAME FOR HOLDING AN ARRAY OF FLEXIBLE TUBING IN ALIGNMENT WITH ONE OR MORE PERISTALTIC PUMP ROTORS

[75] Inventors: Jose C. Deniega, Lake Forest, Calif.; Tsuyoshi Matsumoto, Tokyo, Japan

[73] Assignee: Baxter International Inc., Deerfield, Ill.

[21] Appl. No.: 153,755

[22] Filed: Nov. 17, 1993

[51] Int. Cl.[6] ............................................. F04B 43/08
[52] U.S. Cl. ........................... 417/477.2; 417/477.9; 417/475
[58] Field of Search ............... 417/475, 477 H, 417/477 A, 477 R; 604/174

[56] References Cited

U.S. PATENT DOCUMENTS

| | | | |
|---|---|---|---|
| 3,374,509 | 3/1968 | Logan et al. | 604/174 |
| 3,429,273 | 2/1969 | Jones, Jr. | 417/475 |
| 3,740,173 | 6/1973 | Natelson | 417/475 |
| 3,832,096 | 8/1974 | Gelfand | 417/475 |
| 3,876,340 | 4/1975 | Thomas | 417/475 |
| 3,963,023 | 6/1976 | Hankinson . | |
| 4,205,948 | 6/1980 | Jones . | |
| 4,289,459 | 9/1981 | Neeley et al. | 417/475 |
| 4,385,630 | 5/1983 | Gilcher et al. . | |
| 4,441,867 | 4/1984 | Berelson . | |
| 4,473,342 | 9/1984 | Iles . | |
| 4,544,336 | 10/1985 | Faeser et al. . | |
| 4,564,342 | 1/1986 | Weber et al. . | |
| 4,599,055 | 7/1986 | Dykstra . | |
| 4,619,639 | 10/1986 | Nosé et al. . | |
| 4,776,964 | 10/1988 | Schoendorfer et al. . | |
| 4,824,339 | 4/1989 | Bainbridge et al. . | |
| 4,851,126 | 7/1989 | Schoendorfer . | |
| 4,861,242 | 8/1989 | Finsterwald . | |
| 4,885,001 | 12/1989 | Leppert . | |
| 4,886,431 | 12/1989 | Soderquist et al. | 417/477 |
| 4,909,713 | 3/1990 | Finsterwald et al. . | |
| 4,966,579 | 10/1990 | Polaschegg . | |
| 5,034,135 | 7/1991 | Fischel . | |
| 5,053,127 | 10/1991 | Schoendorfer et al. . | |
| 5,062,774 | 11/1991 | Kramer et al. . | |
| 5,096,393 | 3/1992 | Van Steenderen et al. | 417/475 |
| 5,098,261 | 3/1992 | Bertoncini | 417/475 |
| 5,131,816 | 7/1992 | Brown et al. . | |
| 5,140,747 | 8/1992 | Barnett et al. . | |
| 5,188,588 | 2/1993 | Schoendorfer et al. . | |
| 5,211,548 | 5/1993 | Okada . | |
| 5,257,917 | 11/1993 | Minarik et al. . | |

FOREIGN PATENT DOCUMENTS

| | | |
|---|---|---|
| 1158988 | 12/1983 | Canada . |
| 7721593 | 9/1979 | France . |
| 56-110625 | 9/1981 | Japan . |
| 58-158388 | 9/1983 | Japan . |
| 63-107710 | 5/1988 | Japan . |
| 63-235866 | 9/1988 | Japan . |
| 63-255891 | 4/1990 | Japan . |
| 63-303392 | 6/1990 | Japan . |
| 4-230853 | 8/1992 | Japan . |
| 2246718 | 2/1992 | United Kingdom . |
| WO93/00941 | 1/1992 | WIPO . |

*Primary Examiner*—Richard A. Bertsch
*Assistant Examiner*—Peter G. Korytnyk
*Attorney, Agent, or Firm*—Bradford R. L. Price; Joseph B. Barrett; Daniel D. Ryan

[57] ABSTRACT

A disposable set for a blood processing device comprises an array of flexible tubing and a frame that holds the flexible tubing array with at least two linear segments of the flexible tubing array presented for alignment with at least two axially aligned peristaltic pump rotors.

10 Claims, 9 Drawing Sheets

Fig. 5

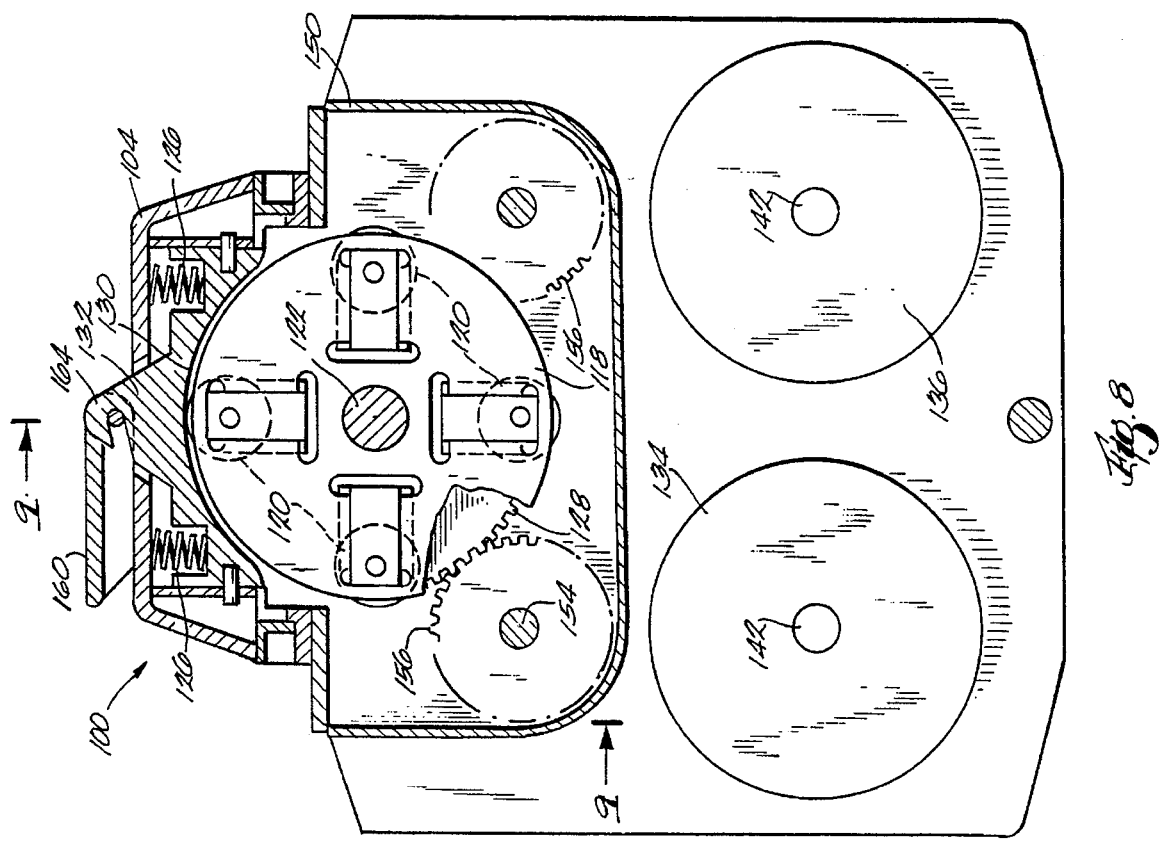
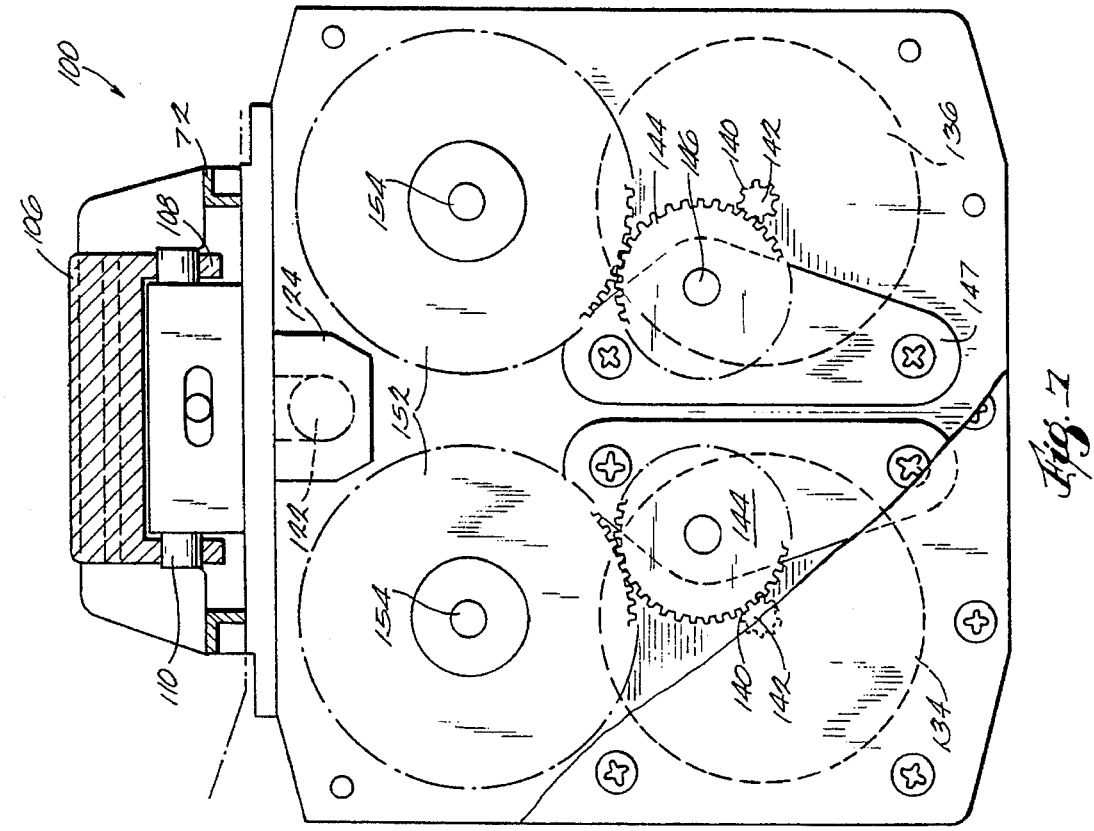

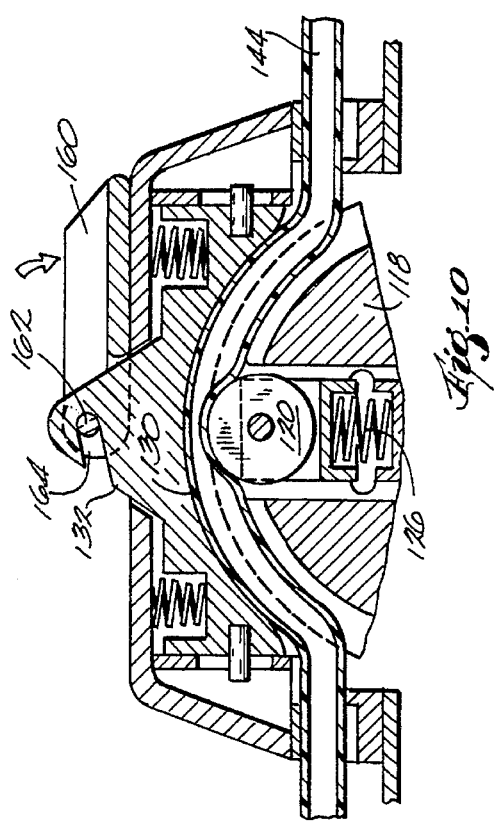
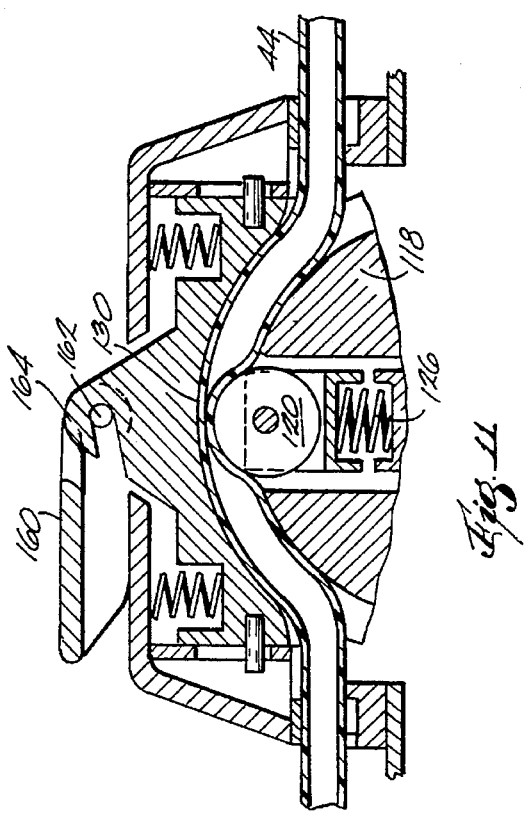
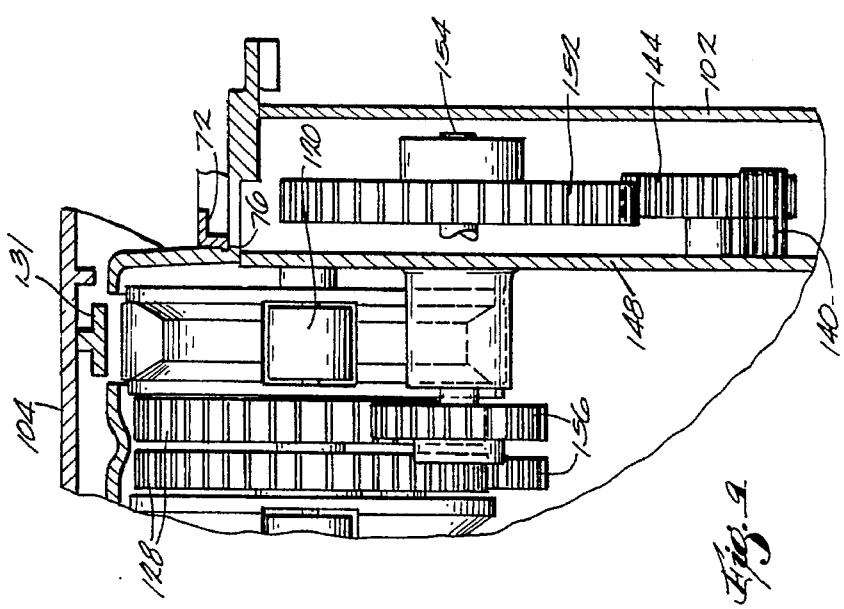

ORGANIZER FRAME FOR HOLDING AN ARRAY OF FLEXIBLE TUBING IN ALIGNMENT WITH ONE OR MORE PERISTALTIC PUMP ROTORS

FIELD OF THE INVENTION

The present invention relates to peristaltic pumps and related apparatus. More particularly, the invention relates to disposable sets for peristaltic pumping apparatus suitable as blood processing devices.

BACKGROUND OF THE INVENTION

Various automated hemapheresis systems for separating whole blood into two or more of its constituents have been utilized in the past. Such devices are shown in Schoendorfer U.S. Pat. No. 4,851,126 and Schoendorfer et al. U.S. Pat. No. 5,188,588, the disclosures of which are incorporated herein by reference.

Such systems are adapted for blood cell separation generally and often specifically for platelet separation. In general, such systems collect whole blood from the donor, separate the desired cells and return the remaining blood components to the donor usually through a single needle. Although a separate return needle can be used, it is preferred that a single venepuncture needle be used both for collection and reinfusion. Hemapheresis systems generally include a disposable set of bags, reservoirs and conduits. The use of peristaltic pumps to cause the blood fluids to move through the system is preferred because the blood and separated blood components can be moved through the device while it is wholly contained within the sterile disposable components, which are commonly referred to as a harness set. Harness sets include, at least, one venepuncture needle, at least one separation device for separating blood into its components, and at least one reservoir for containing blood. A plurality of conduits connect the needle, the separation device and the reservoir to each other. The conduits include a section formed of flexible elastomeric material so that blood can be moved through the conduits by means of peristaltic roller pumps.

The preferred type of system includes, as a minimum, a single venepuncture needle, separation means for separating at least one constituent from whole blood, first and second reservoirs containing blood, a first conduit interconnecting the needle and the first reservoir, a second conduit interconnecting the first reservoir and the separation means, a third conduit interconnecting the separation means and the second reservoir, and a fourth conduit for returning blood components to the needle. Preferably, four separate peristaltic pumps are provided to move the blood and the blood components through the conduits.

Typically, systems of this general type also include a microprocessor for controlling a number of pumps, clamps, detectors, monitoring systems, et cetera, for automating the collection of whole blood from the donor, separating the blood into plasma and cell concentrate, collecting the plasma and reinfusing the cell concentrate into the donor using the harness set applied to the instrument. After application of venepuncture to the blood donor, the instrument operates between alternating collection and reinfusion cycles. In the collection cycle, anticoagulated whole blood in pumped by a blood pump to the separator of the harness where it is separated into plasma which flows into a collection container and cell concentrate which flows to a reinfusion reservoir. In the reinfusion cycle, the blood pump reverses to flow cell concentrate from the reservoir through the phlebotomy needle to the donor.

Peristaltic pumps are also used for the delivery of other liquids such as medications, additives to fluid mixing processes, etc. A need has continued to exist for such apparatus that is compact and easy to use and for improved disposable conduit or harness sets for use in conjunction with such apparatus.

SUMMARY OF THE INVENTION

The invention provides a frame for holding an array of flexible tubing. The frame holds the flexible tubing array with at least two linear segments of the flexible tubing array presented for alignment with at least two axially aligned peristaltic pump rotors.

In a preferred embodiment, the frame also includes means for holding at least one segment of the flexible tubing array for alignment with a tube clamp or sensing device while the other at least two segments are presented for alignment with the pump rotors.

These and further objects and advantages of the present invention will become more apparent on reference to the following detailed description, appended claims and drawings.

BRIEF DESCRIPTION OF THE DRAWINGS

FIG. 5 is a perspective view of a device in accordance with the invention with the harness set installed;

FIG. 7 is a cross-sectional view taken along line 7—7 of FIG. 6;

FIG. 8 is a cross-sectional view taken along line 8—8 of FIG. 6;

FIG. 9 is a cross-sectional view taken along line 9—9 of FIG. 8;

FIG. 10 is a fragmentary sectional view of a pump assembly taken along line 10—10 of FIG. 6 with blood flow tubing added and with an individual release mechanism in the open position;

FIG. 11 is a fragmentary cross-sectional view taken along line 10—10 of FIG. 6 showing the individual release mechanism in the closed position, also showing the blood flow tubing;

DETAILED DESCRIPTION OF THE DRAWINGS

Figure 1:
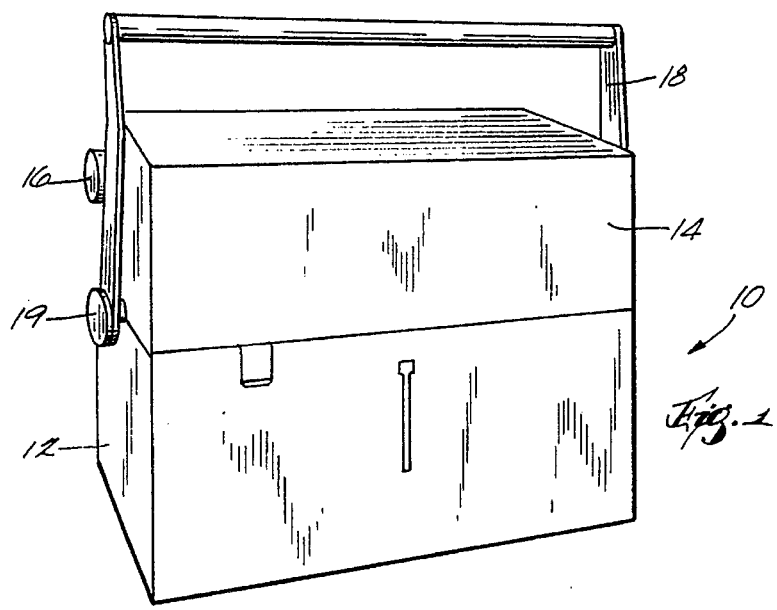
FIG. 1 is a perspective view of a portable hemapheresis device of the present invention with the cover in the closed position.

Referring now to the drawings, there is illustrated a portable hemapheresis device, generally designated 10. Device 10 includes a bottom portion 12 and a cover portion 14 hinged along an axis 16. A carrying handle 18 is provided which is hingedly connected to bottom portion 12 at hinge points 19.

Figure 2:
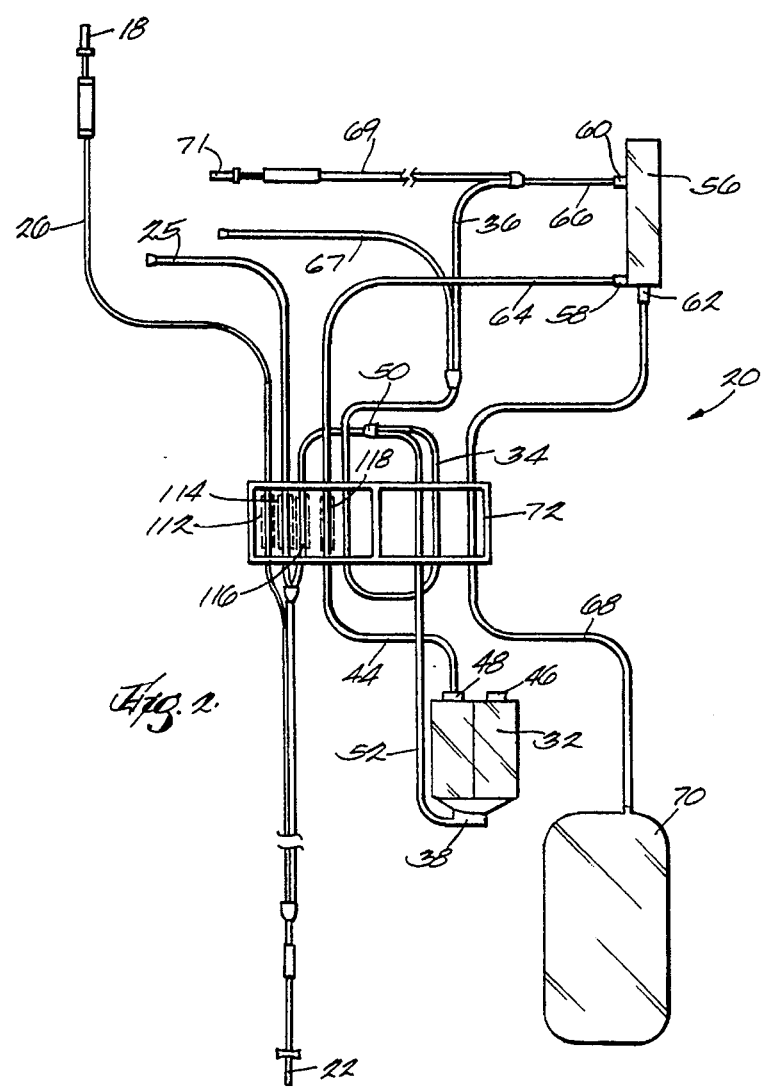
FIG. 2 is a top plan view of an embodiment of a harness set usable in connection with the present invention.
Figure 3:
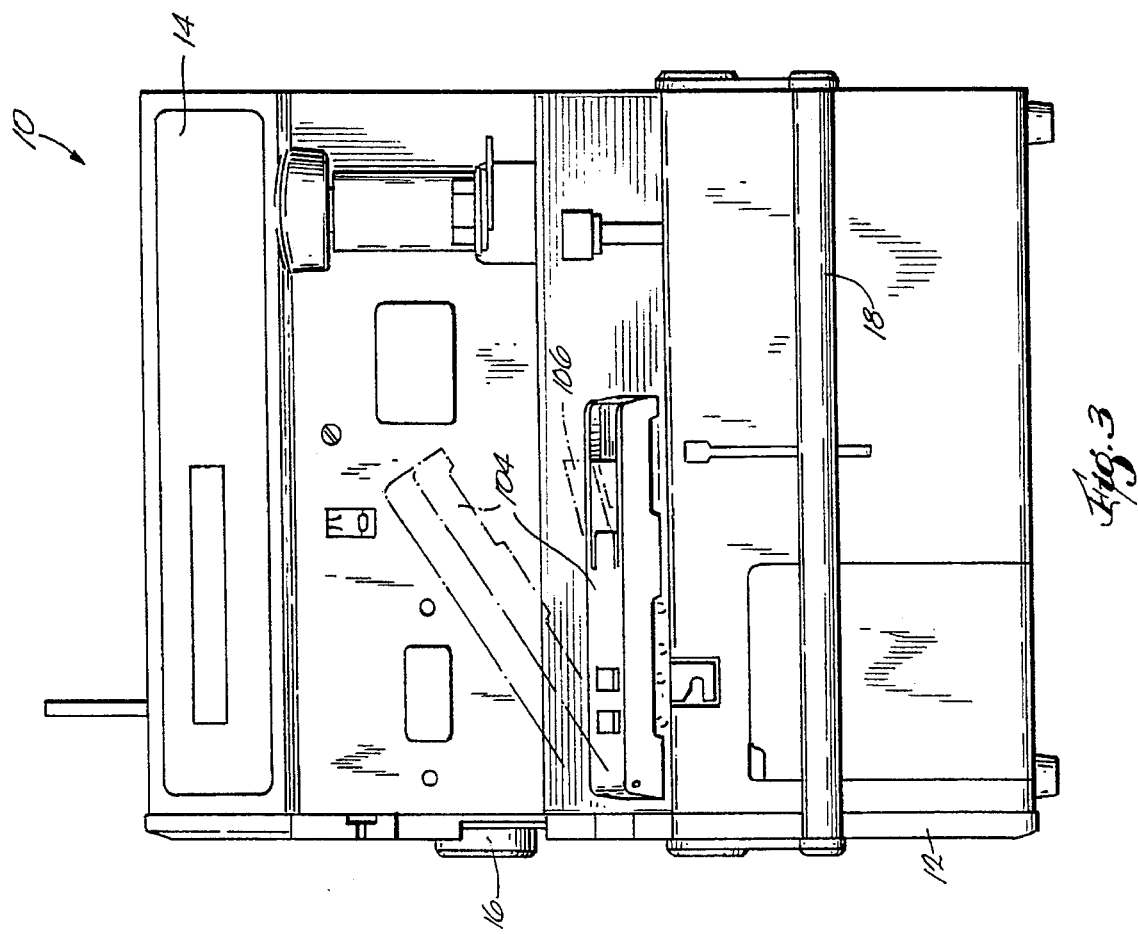
FIG. 3 is a front elevational view of a device in accordance with the invention with the pump module cover in the closed position and illustrating the open position of the cover by means of phantom lines.
Figure 4:
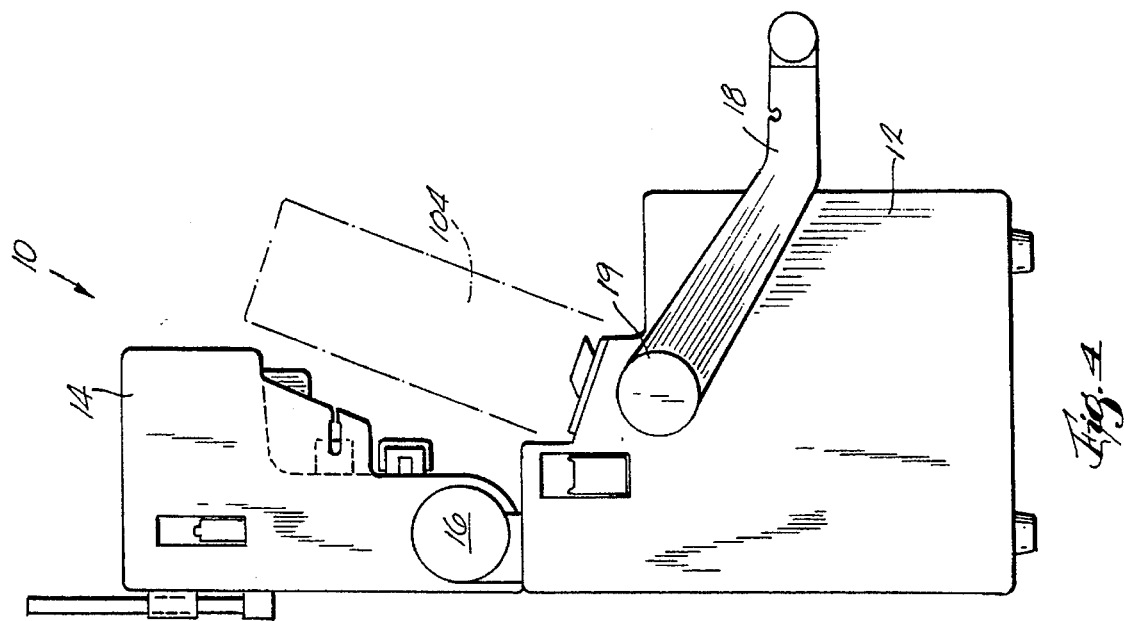
FIG. 4 is an end view of the device of FIG. 3.
Figure 5:
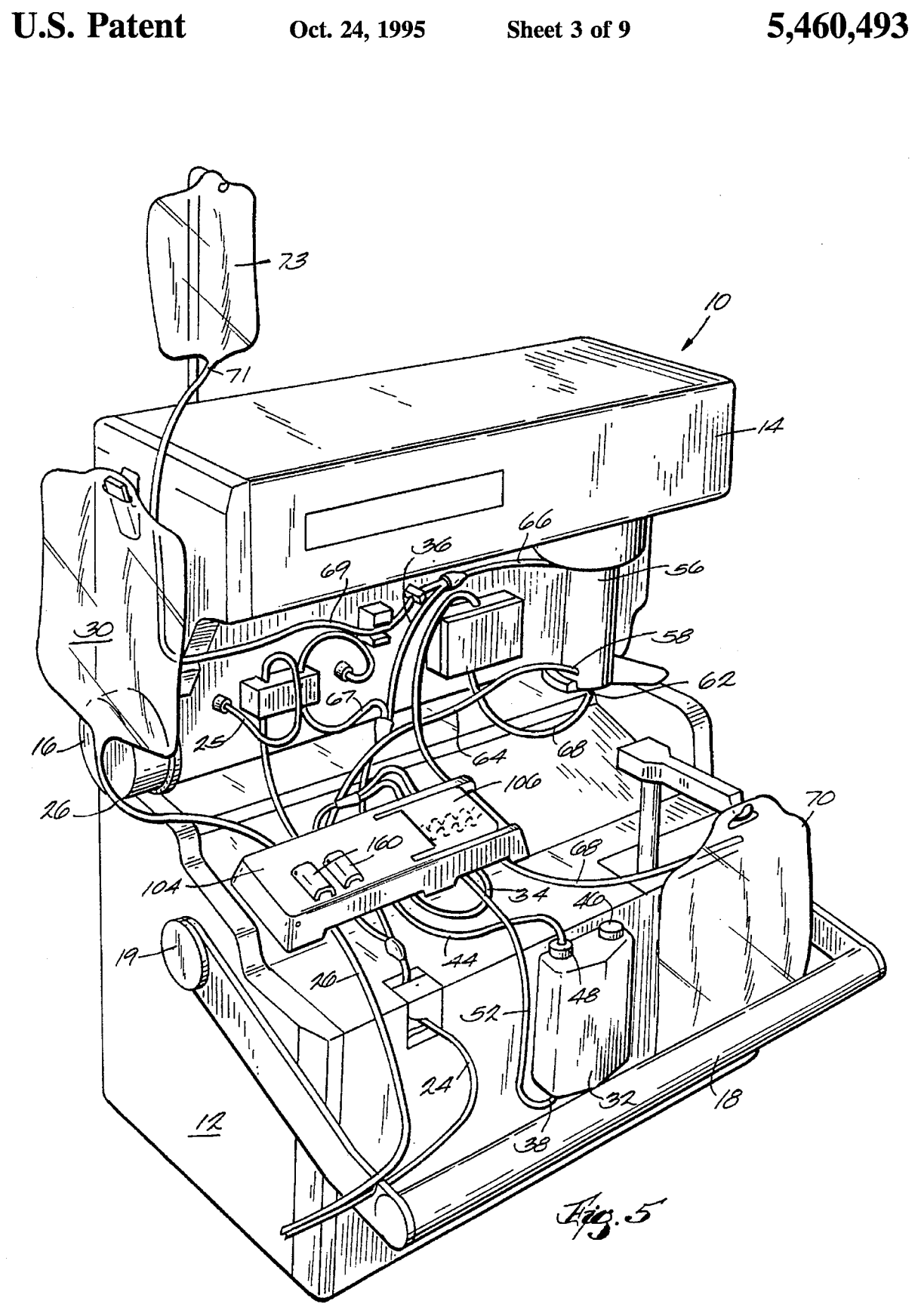

Referring to FIG. 2, there is illustrated a disposable tubing or harness set generally designated 20. In accordance with the invention, harness set 20 is applied to the hemapheresis device as illustrated in FIG. 5 to effect collection of whole blood from a donor through a single needle, separation of the whole blood into packed' blood cells and platelet poor plasma, and reinfusion of the packed blood cells to the donor.

Tubing set 20 is provided with a single venepuncture needle set 22 for alternately receiving whole blood from a donor and reinfusing packed cells into the donor. Venepuncture needle set 22 communicates with a blood line 24. An anticoagulant line has an anticoagulant spike 18 at one end for reception in an anticoagulant supply container 30 illustrated in FIG. 5. At its opposite end, anticoagulant line 26 joins blood line 24 in a Y-connection closely adjacent the single venepuncture needle 22.

Tubing set 20 also includes a reservoir 32. Blood line 24 is connected through port 38 at the lower end of the reservoir 32. Tube 44 extends into reservoir 32 through an inlet port 48 at the upper end of reservoir 32. Blood line 24 branches at a Y-connection 50 to branch line 52 connecting blood line 24 with inlet port 38 of reservoir 32, and to branch line 34 connecting blood line 24 to separator inlet 60.

Tubing set 20 additionally includes a separator 56 for separating anticoagulated whole blood into packed cells and plasma. Such separators are preferably of a membrane type, known in the art. Separator 56 has a whole blood inlet port 60, a packed cell outlet port 58 and a platelet poor plasma outlet port 62. Line 64 connects the packed cell inlet port 48 of reservoir 32 with the outlet port 58 of separator 56. Conduit line 66 connects the whole blood inlet port 60 of separator 56 by means of Y-connections as shown with tubing 24. By means of a Y-connection tubing 66 is also connected by tubing 69 to a saline bag spike 71. Lines 25 and 67 lead to pressure sensors. Tubing 68 connects between the plasma outlet port 62 of separator 56 and a plasma collection container 70.

A tubing organizer 72, which may be formed either of solid or cellular plastic material, in the form of a rectangular frame open in the middle, is provided to hold the various tubing in a desired orientation. The tubing is snapped in place into slots 74 provided in the plastic material. The segments of the various tubes interacting with the pump assembly are, thus, positioned in registry in relation to the pumps. The organizer can remain in place during the pumping operation, and the tubing can conveniently be removed as a unit. Preferably the organizer 72 is of an L-shaped configuration to provide physical stability and resistance to twisting. Lips 76 can be provided to snap into mating recesses in the cover of the pump assembly as further explained below.

It is further contemplated that a second, alternative, tubing set may also be employed substantially as described in U.S. Pat. No. 4,851,126. The second tubing portion is generally utilized in order to further separate the blood into platelet concentrate and platelet poor plasma. The alternative tubing set is applied to the pump assembly of the present device in a manner similar to that described above in relation to the plasma collection tubing set described above.

Referring to FIGS. 3, 4 and 6–12, the pump module assembly generally identified by numeral 100 is shown in greater detail. A housing 102 is provided within bottom portion 12 of the hemapheresis device. Housing 102 is provided with a cover 104 pivotally attached to a bracket 105. Cover 104 is releasably locked in a closed position by means of handle 106 provided with a clevis 108 that engages opposite ends of a pin 110. Mounted in the upper part of housing 102 are a series of peristaltic pump rotor assemblies 112, 114, 116 and 118, hereinafter referred to as "pumping modules", all of which are mounted on a single axle 122. Each of these pumping modules is provided with a plurality of rollers 120, of which there are four in the illustrated embodiment. Shaft 122 is journaled at its opposite ends in a bearing structure 124 provided at opposite ends of housing 102. Each of the rollers 120 is outwardly biased by compression springs 126.

Figure 6:
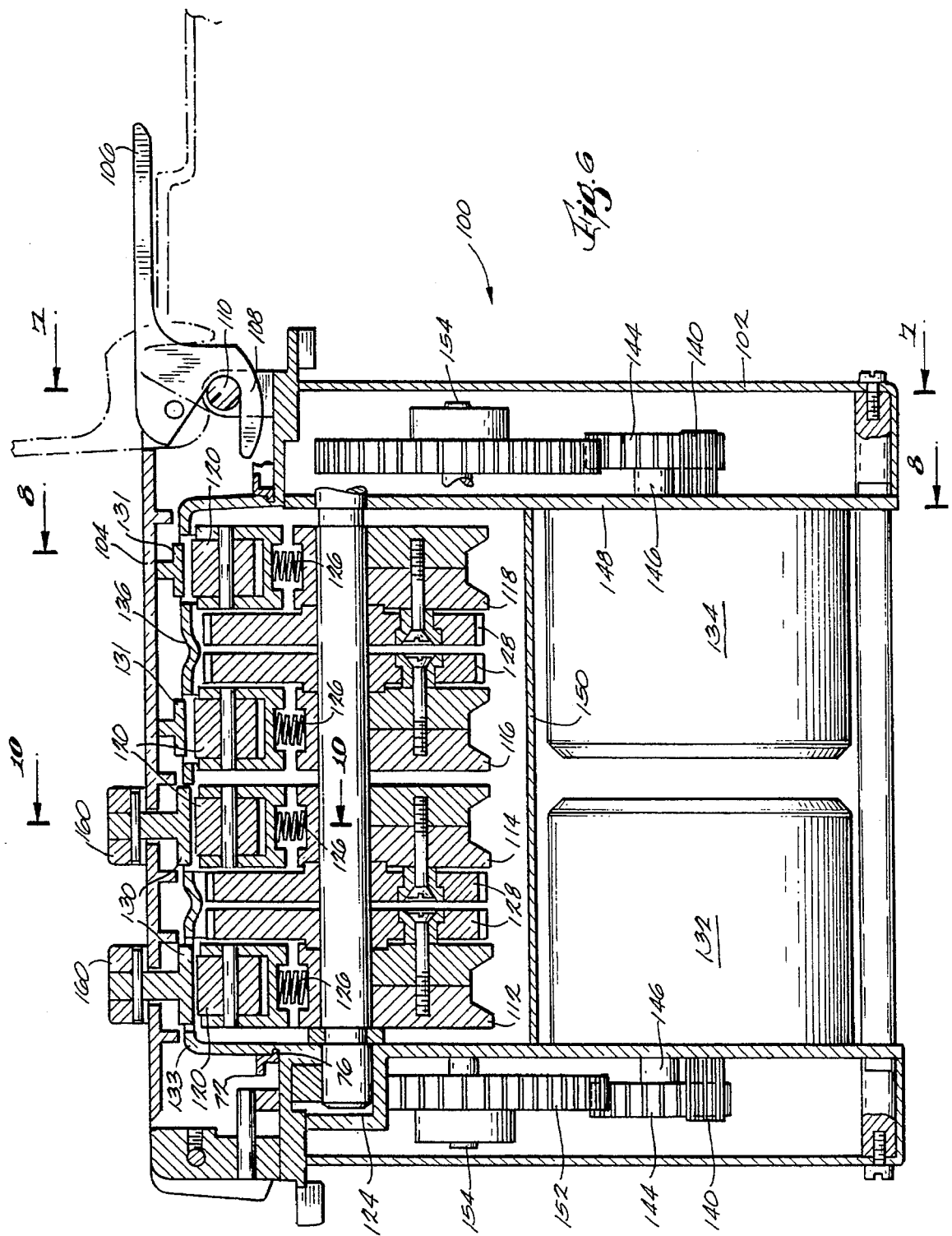
FIG. 6 is a cross-sectional view of a pump module assembly in accordance with the invention taken the central shaft of the assembly.

As seen in FIG. 6, the roller pump rotors may each be formed of two-part sheaves to which drive gears 128 are bolted. Releasable race surfaces 130 and stationary race surfaces 131 are provided to backstop the blood flow conduits when they are worked on by rollers 120 as best seen in FIGS. 10 and 11. The compression of the flexible tubes by the rollers 120 of the pumps provides a peristaltic pumping action which moves fluid through the conduits. Reversible DC motors 132, 134, 136 and 138 (not shown) are provided to reversibly drive each of the pumping modules 112, 114, 116 and 118. Gears 140 are attached to the motor shafts 142. Each of the gears 140 meshes with a driven gear 144 each of which are mounted on shafts 146 journaled for rotation through a supporting bracket 147. Gears 144 in turn drive gears 152 which are mounted on shafts 154 which are journaled for rotation through end walls 148 of housing 150. At the opposite ends of shafts 154 are mounted drive gears 156 which mesh with and drive gears 128 on each of the pumping modules.

While the embodiment shown in the drawings illustrates the same gear ratios between each of the motors and its respective pumping module, it will be apparent that the gear ratios can be varied if it is desired that one of the pumping modules 112, 114, 116 or 118 be driven at a speed different from that of the other of said pumping modules. Also it is contemplated that a different number of pumps, for example 2 or 6 can be incorporated into the pump assembly. An assembly of four pumps is shown solely for purposes of illustration.

Figure 12:
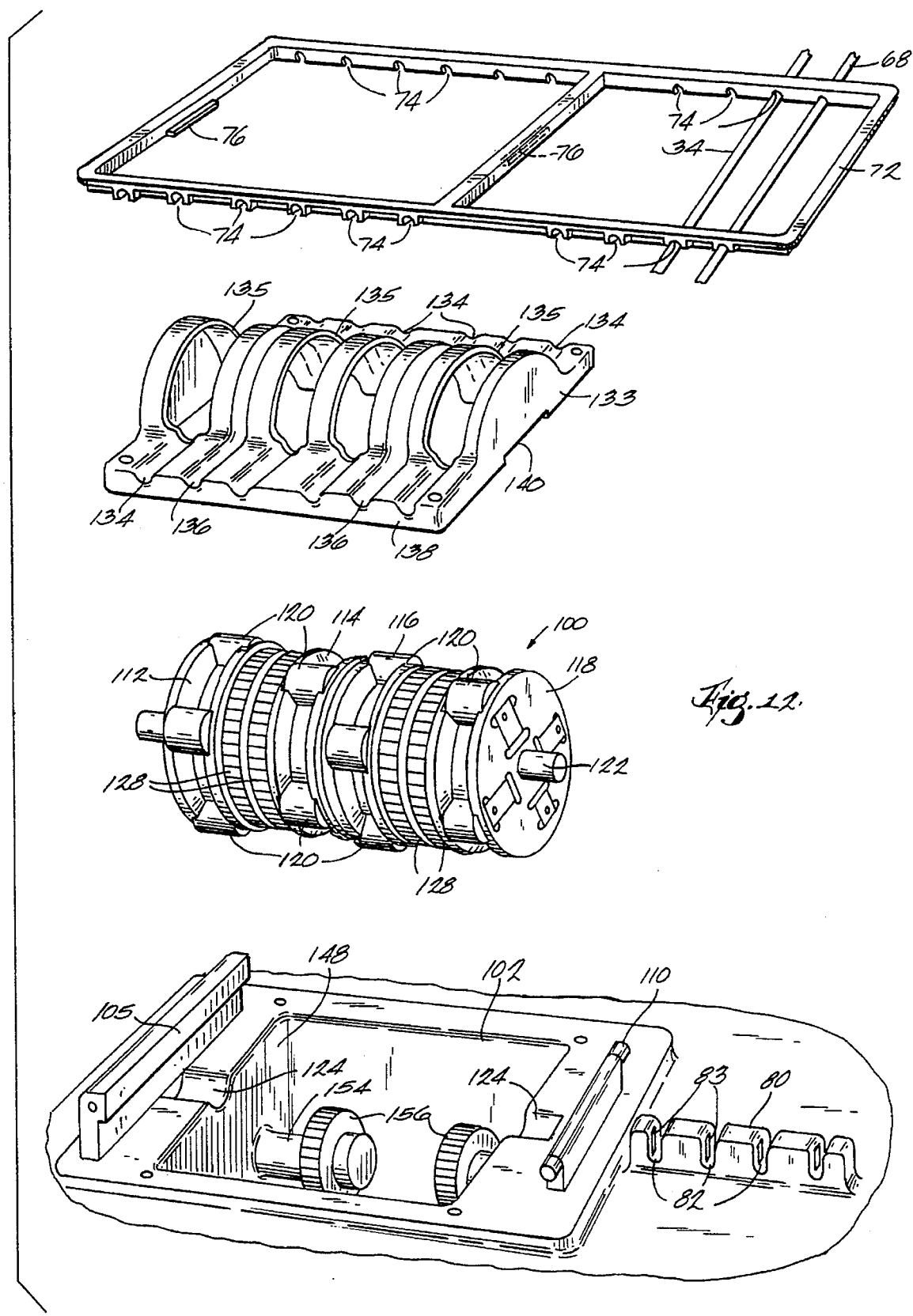
FIG. 12 is a perspective view of the pump module assembly and organizer frame components of the invention shown separated from each other for clarity.

By opening lever 106 the axle 122 and each of the pumps mounted on it can be removed as a unit as best seen in FIG. 12. For example, in the event of a blood spill the entire assembly can be removed with one hand for cleaning, or otherwise, for maintenance. Additionally, each of the concave race surfaces 130 can be individually released as shown in FIGS. 8, 10 and 11. Individual release mechanisms are provided by the use of release handles 160 which are pivotally attached to a rod 162 carried on cover 104. An eccentric end 164 of lever 160 bears against the upper surface of each individual member 132, the lower end of which forms race 130. Thus, when the lever 160 is in the closed position illustrated in FIG. 11, the roller 120 flattens conduit 44 between the roller and race surface 130, thus, causing blood to be moved through conduit 44 in peristaltic fashion as the roller 120 is advanced. In the released position shown in FIG. 10, the flow of blood through conduit 44 can be interrupted. The ability to individually release the pumping modules is useful for system fault isolation, emergencies, and other non-programmed operational modes.

Figure 13:
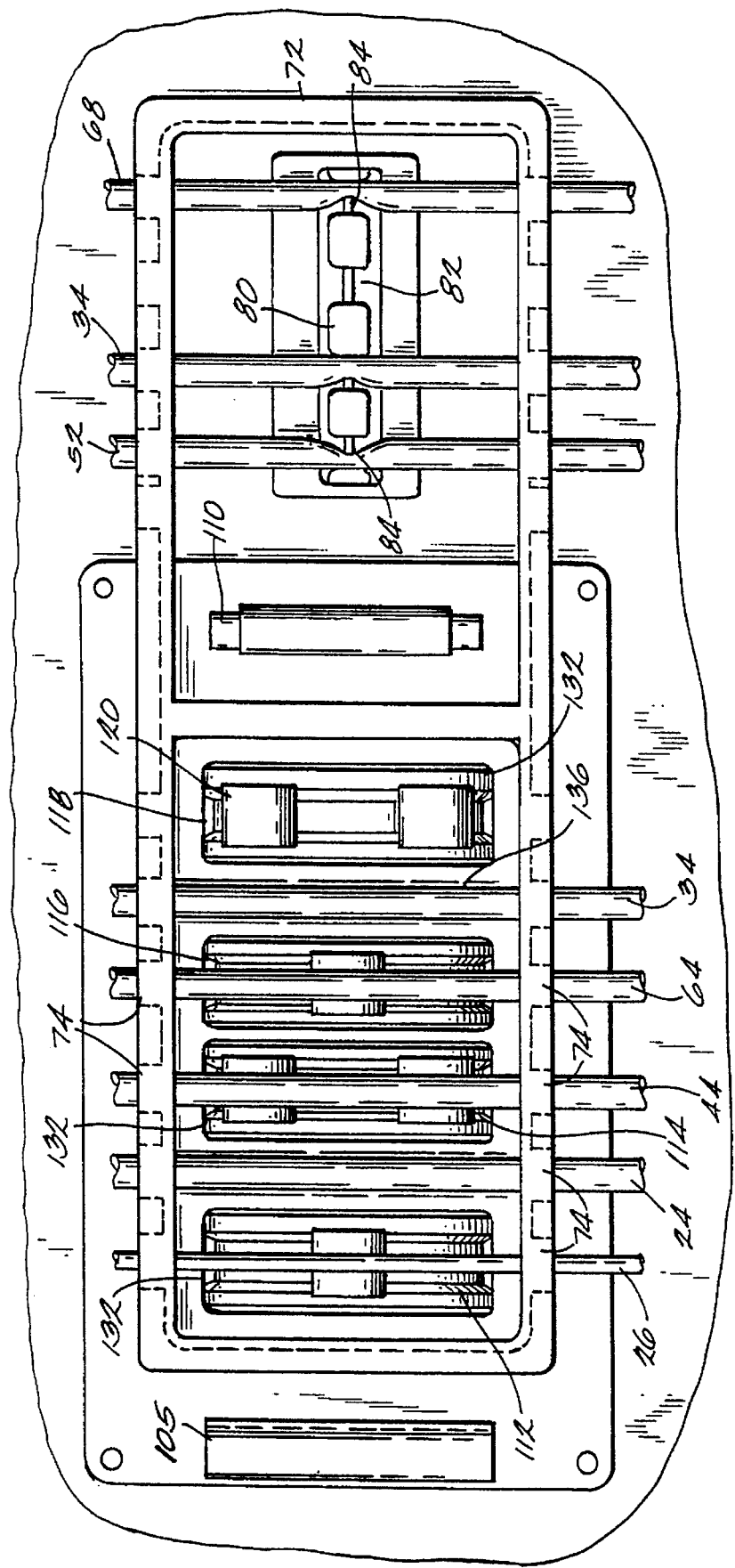
FIG. 13 is a top plan view of the pump module assembly showing the organizer and blood tubes in place over the pumps.

The relationship of organizer 72 with the pump module assembly 100 is best seen by referring to FIGS. 12 and 13. An internal cover 133 is positioned over pump module assembly 100. Internal cover 133 has a series of openings 135 through which the rollers 120 are exposed. Indented channels 134 are aligned with openings 135 to receive the various blood tubes. Additional indented grooves 136 are provided over the entire transverse width of cover 133 to accommodate blood tubing that is not to be engaged or acted on by any of the peristalsis pumps. Cover 133 is further provided with exterior shoulders 138 that closely interfit with the interior surfaces of organizer frame 72. Placement of the frame 72 over cover 133, thus, provides a mating fit by virtue of which the blood tubes are placed in precise registry with grooves 134 or 136, as required. Organizer frame 72 is provided with projecting lips 76 that engage recesses 140 at the opposite ends of cover 133 to positively allow the organizer frame 72 to be snapped and held in place.

Figure 14:
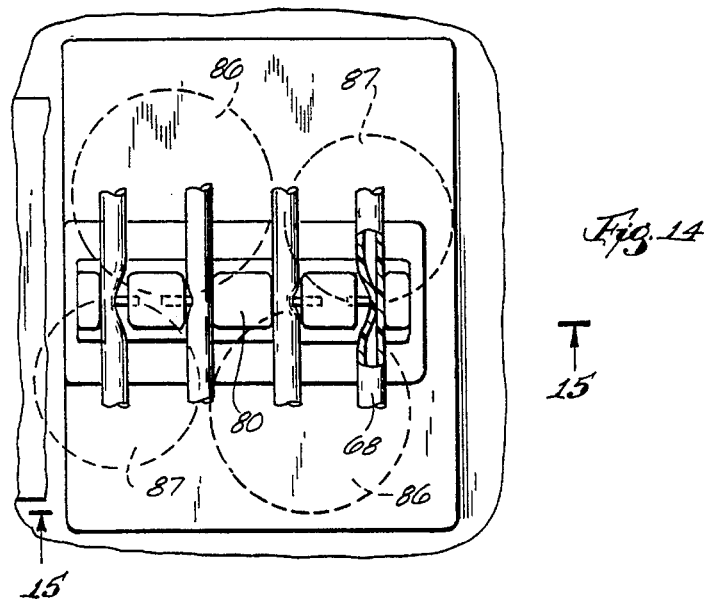
FIG. 14 is a top plan view showing tubing clamps used in the device of the invention.
Figure 15:
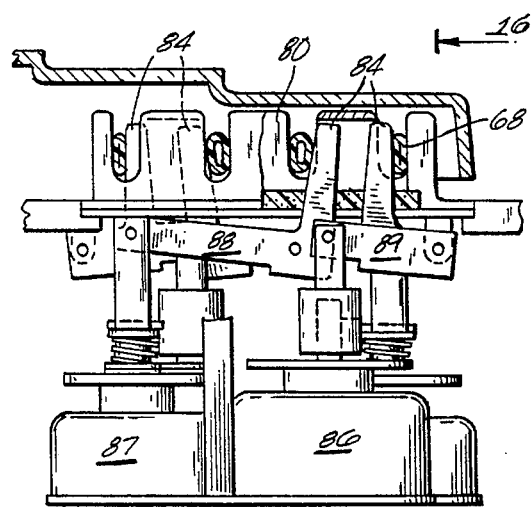
FIG. 15 is a cross-sectional view taken along line 15—15 of FIG. 14.
Figure 16:
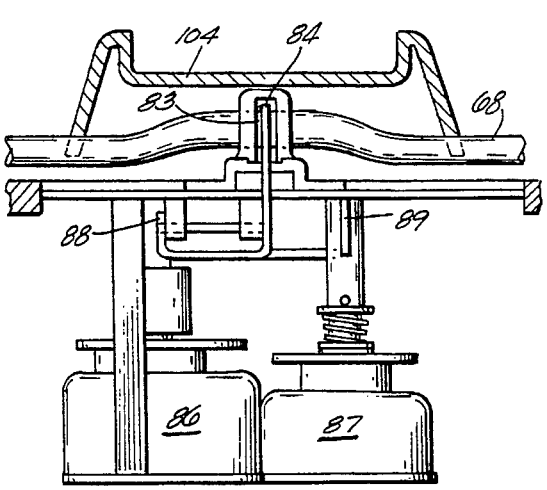
FIG. 16 is a cross-sectional view taken along line 16—16 of FIG. 15.

In addition to pump module assembly 100, cover 104 overlies projecting element 80 that is provided with a series of slots 82. Slots 82 are provided with lateral openings 83 which accommodate clamp fingers 84 that, if required, can clamp off conduits 34, 52 and 68 as seen in FIGS. 14–16. Fingers 84 can be operated by rocker arms 88 and 89 which are actuated by solenoid valves 86 and 87 each controlled by software that operates each of the successive operations of apparatus 10. Thus, for example, when blood is being reinjected into the patient, tubing 34 is clamped closed so that saline solution cannot enter tubing 24. Similar clamping or unclamping steps will be apparent to those skilled in the art. Instead of clamp fingers 84 a sensing device can be substituted to assist in monitoring the flow through the conduits as will be appreciated by those skilled in the art.

It will be noted in connection with the preferred embodiment that pump drive motors 134 and 136 are approximately half of the length of the pump module, thus, allowing four motors to be located under the pump module assembly. The gear reduction assembly has symmetry about the center plane of the pump module assembly and is located outside of the housing 150. Shafts 154 are provided with seals to prevent blood or other fluids from entering the main body of the machine from within housing 150 in the event of a spill. It will be noted that since the pumping modules are radially removable from the gear train, they are removable for cleaning and maintenance without disturbing the balance of the equipment.

While the invention has been described in connection with the foregoing specific embodiment, it is to be understood that the invention is not to be limited thereto, but on the contrary it is intended to cover various modifications and equivalent arrangements included within the spirit and scope of the appended claims.

What is claimed is:

1. A disposable set for a blood processing device comprising an array of flexible tubing and a generally rectangular frame having means for holding the flexible tubing array with at least two linear segments of the flexible tubing array represented for alignment with at least two peristaltic pump rotors, said rotors being contained in a housing and extending upwardly through the top of said housing and being axially aligned with each other, an outer cover and an inner cover located over the top of said housing, said inner cover extending around said rotors and extending from said top of said housing toward said outer cover, said inner cover having channels in its periphery aligned with said rotors, whereby flexible tubing placed over said inner cover in said channels is aligned with said rotors, said inner cover being sized to closely interfit with said rectangular frame to place said tubing in registry with said rotors.

2. A set according to claim 1 wherein the frame also includes means for holding at least one segment of the flexible tubing array for alignment with a tube clamp while the other at least two segments are presented for alignment with the pump rotors.

3. Apparatus according to claim 1 wherein said holding means of said frame comprises indentations aligned with said channels in said inner cover.

4. A set according to claim 3 wherein said frame is provided with an inwardly extending lip engageable in a mating recess in said inner cover.

5. A disposable set for use in conjunction with a peristaltic pump assembly that includes a housing having a top opening, a peristaltic rotor pumping module carrying a plurality of rotatable rollers spaced around its periphery, said rotor being mounted for rotation on an axle and having a central plane normal to said axle, a motor for driving said rotor operatively connected to said rotor, wherein said axle is mounted parallel to the top of said housing, said rotor extending through the top of said housing, said housing further having a cover pivotally mounted thereon, said cover carrying a concave race in alignment with and engageable by said rollers to activate peristaltic liquid flow in a flexible conduit positioned between said rotor and said race, said cover being pivotable from an operative position wherein said race engages said rollers to an inoperative position wherein said rotor is exposed for loading and unloading a conduit between said rotor and said race, said disposable set comprising a plurality of flexible conduits and an organizer frame adapted to fit under said cover and being provided with indentations for receiving and positioning at least one segment of said flexible fluid flow conduits and for aligning said segment with said pumping module, and means on said housing for positioning said frame thereon so that said conduit is aligned with said rotor said means including indentations on opposite sides of said rotor to assist in alignment of said conduit with said rotor.

6. A disposable set according to claim 5 wherein said means for positioning comprises a shoulder provided on said housing engageable by said organizer frame.

7. A set according to claim 6 wherein said organizer frame is provided with an inwardly extending lip engageable in a mating recess in said shoulder.

8. A disposable set according to claim 5 comprising means for separating blood received from a donor into constituents, including:

means for separating at least one blood constituent from whole blood;

a reservoir for containing blood;

a single venepuncture needle for supplying whole blood to the reservoir during a whole blood collection cycle and reinfusing blood from the reservoir into the donor during a reinfusion cycle;

a plurality of flexible blood flow conduits for conveying whole blood and blood constituents between the donor, said reservoir and said means for separating blood said organizer frame engaging a plurality conduit segments and aligning them with a plurality of axially aligned peristaltic pumping modules for engaging said conduits and for activating the flow of blood through said conduits.

9. A set according to claim 5 wherein said frame is also provided with indentations for receiving and positioning a segment of a flexible fluid flow conduit and for aligning said segment with a clamp for closing said conduit said clamp being positioned adjacent to the pumping module assembly.

10. Apparatus according to claim 5 further comprising an inner cover positioned on the top of said housing and extending around said rotor, said inner cover having channels in its periphery aligned with the central plane of said rotor, whereby a flexible conduit placed over said inner cover in said channels is aligned with said rotor, said inner cover being sized to closely interfit with said frame to place said conduit in registry with said pumping module.

* * * * *